(12) United States Patent
Kurashima et al.

(10) Patent No.: US 11,866,497 B2
(45) Date of Patent: Jan. 9, 2024

(54) ANTIBODY TO FIBROSIS-RELATED MOLECULE AND MEDICAL APPLICATION THEREOF

(71) Applicant: The University of Tokyo, Tokyo (JP)

(72) Inventors: Yosuke Kurashima, Tokyo (JP); Hiroshi Kiyono, Tokyo (JP)

(73) Assignee: The University of Tokyo, Tokyo (JP)

( * ) Notice: Subject to any disclaimer, the term of this patent is extended or adjusted under 35 U.S.C. 154(b) by 175 days.

(21) Appl. No.: 17/399,725

(22) Filed: Aug. 11, 2021

(65) Prior Publication Data

US 2022/0033498 A1     Feb. 3, 2022

Related U.S. Application Data

(62) Division of application No. 16/465,253, filed as application No. PCT/JP2017/043348 on Dec. 1, 2017, now Pat. No. 11,117,962.

(30) Foreign Application Priority Data

Dec. 2, 2016 (JP) ................................ 2016-234717

(51) Int. Cl.
| | |
|---|---|
| *G01N 33/53* | (2006.01) |
| *C07K 16/28* | (2006.01) |
| *A61P 29/00* | (2006.01) |
| *G01N 33/68* | (2006.01) |
| *A61K 39/00* | (2006.01) |

(52) U.S. Cl.
CPC .......... *C07K 16/2803* (2013.01); *A61P 29/00* (2018.01); *G01N 33/6854* (2013.01); *A61K 2039/505* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 9,612,248 B2 * | 4/2017 | Nikrad | ............... G01N 33/6893 |
| 2014/0303018 A1 | 10/2014 | Nikrad et al. | |
| 2015/0072879 A1 | 3/2015 | Princen et al. | |

FOREIGN PATENT DOCUMENTS

| | | |
|---|---|---|
| CN | 103278624 A | 9/2013 |
| JP | 2015-502740 A | 1/2015 |

OTHER PUBLICATIONS

Andoh et al., "Molecular Biology of Intestinal Subepithelial Myofibroblasts and Inflammation," The 15th New Molecular Biology of the Digestive Tract, G.I. Research, 2011, 19(1):99-105, with non-official English translation, 1-13.
Buhusi et al,. "Close Homolog of L1 is an Enhancer of Integrin-mediated Cell Migration," The Journal of Biological Chemistry, Jul. 4, 2003, 278(27):25024-25031.
Dong et al., "Single-Chain Variable Fragment Antibodies Against the Neural Adhesion Molecule CHL1 (Close Homolog of L1) Enhance Neurite Outgrowth," Journal of Neuroscience Research, 2002, 69:437-447.
Final Office Action on U.S. Appl. No. 16/465,253 dated Jan. 21, 2021.
Huang et al., "Loss of cell adhesion molecule CHL1 improves homeostatic adaptation and survival in hypoxic stress," Cell Death and Disease, 2013, 4, e768, 9 pages.
International Search Report dated Feb. 27, 2018, in PCT/JP2017/043348, with English translation.
Non-Final Office Action on U.S. Appl. No. 16/465,253 dated Jun. 29, 2020.
Notice of Allowance on U.S. Appl. No. 16/465,253 dated May 12, 2021.
Restriction Requirement in U.S. Appl. No. 16/465,253 dated Apr. 7, 2020.
Thelen et al., "The Neural Cell Adhesion Molecule L1 Potentiates Integrin-Dependent Cell Migration to Extracellular Matrix Proteins," The Journal of Neuroscience, Jun. 15, 2002, 22(12):4918-4931.
Wei et al., "In silico-initiated cloning and molecular characterization of a novel human member of the L1 gene family of neural cell adhesion molecules," Hum. Genet., 1998, 103:355-364.
Wolterink et al., "Therapeutic Antibodies to Human L1CAM: Functional Characterization and Application in a Mouse Model for Ovarian Carcinoma," Cancer Research, 2010, 70(6):2504-2515.
Yamanaka et al., "Increase of Close Homolog of Cell Adhesion Molecule L1 in Primary Afferent by Nerve Injury and the Contribution to Neuropathic Pain," J. Comp. Neurol., 2011, 519:1597-1615.

\* cited by examiner

*Primary Examiner* — Maher M Haddad
(74) *Attorney, Agent, or Firm* — Foley & Lardner LLP

(57) ABSTRACT

The present invention provides an antibody to a fibrosis-related molecule and medical application thereof. The antibody of the present invention is an antibody that binds to CHL1 protein and an antibody that neutralizes the binding of the CHL1 protein to a fibroblast.

6 Claims, 10 Drawing Sheets

Specification includes a Sequence Listing.

Mouse large intestine tissue

Human Crohn disease large intestine sample

Healthy human subject	Crohn disease

ANTIBODY TO FIBROSIS-RELATED MOLECULE AND MEDICAL APPLICATION THEREOF

CROSS-REFERENCE TO RELATED APPLICATIONS

This application is a Divisional of U.S. application Ser. No. 16/465,253, which is the U.S. National Stage of PCT/JP2017/043348, filed Dec. 1, 2017, which claims priority to JP 2016-234717, filed Dec. 2, 2016.

The instant application contains a Sequence Listing which has been submitted in ASCII format via EFS-WEB and is hereby incorporated by reference in its entirety. Said ASCII copy, created on Aug. 10, 2021, is named sequence.txt and is 4,141 bytes.

TECHNICAL FIELD

The present invention relates to an antibody to a fibrosis-related molecule and medical application thereof.

BACKGROUND ART

Inflammation is necessary as a repair process of tissue damage. However, inflammation may not disappear after the repair of the tissue. In such inflammation, fibroblasts are activated so that the amount of collagen excreted is elevated, leading to the risk of causing fibrosis of the tissue.

Tissue fibrosis is irreversible and cannot be treated. Therefore, it is important to prevent fibrosis from occurring. Thus, there exist needs for an approach of diagnosing fibrosis or an approach of preventing fibrosis.

CHL1 is known as a cell adhesion molecule analogous to a brain neural cell adhesion factor L1 (Non Patent Literature 1). However, its physiological functions are hardly known.

CITATION LIST

Non Patent Literature

Non Patent Literature 1: MH Wei et al., Hum. Genet. 103, 39: 355-364, 1998

SUMMARY OF INVENTION

Technical Problem

The present invention provides an antibody to a fibrosis-related molecule and medical application thereof.

Solution to Problem

The present inventors have identified CHL1 as a factor specifically expressed at the acute phase and chronic phase of inflammation. The present inventors have revealed that: CHL1 is presented on the membrane surface of fibroblasts; and secreted CHL1 binds to a non-immune and non-epithelial non-hemocyte cell, such as a myofibroblast, of the lamina propria and a submucosal layer. The present inventors have also found that: an anti-CHL1 antibody delays tissue repair ascribable to fibroblasts at the acute phase of inflammation, and can suppress excessive collagen production and the activity of fibroblasts at the chronic phase of inflammation. The present inventors have further found that the expression of CHL1 is sustained not only at the acute phase but at the chronic phase of inflammation, and found that the administration of an anti-CHL1 antibody after the acute phase of inflammation causes suppression of collagen deposition and fibroblast activation.

Specifically, the present invention provides the following aspects:

[1] An antibody that binds to CHL1 protein, or an antigen-binding fragment thereof, wherein the antibody or the antigen-binding fragment thereof neutralizes the binding of the CHL1 protein to a non-immune and non-epithelial non-hemocyte cell of the lamina propria and a submucosal layer.

[2] An antibody that binds to CHL1 protein, or an antigen-binding fragment thereof, wherein the antibody is (1) an antibody having a heavy chain variable region having heavy chain CDR1 having the amino acid sequence set forth in SEQ ID NO: 1, heavy chain CDR2 having the amino acid sequence set forth in SEQ ID NO: 2 and heavy chain CDR3 having the amino acid sequence set forth in SEQ ID NO: 3, and a light chain variable region having light chain CDR1 having the amino acid sequence set forth in SEQ ID NO: 5, light chain CDR2 having the amino acid sequence set forth in SEQ ID NO: 6 and light chain CDR3 having the amino acid sequence set forth in SEQ ID NO: 7, or (2) an antibody that competes with the antibody (1) for binding to the CHL1 protein.

[3] The antibody or the antigen-binding fragment thereof according to [2], wherein the antibody is (3) an antibody having a heavy chain variable region having the amino acid sequence set forth in SEQ ID NO: 4 and a light chain variable region having the amino acid sequence set forth in SEQ ID NO: 8, or (4) an antibody that competes with the antibody (3) for binding to the CHL1 protein.

[4] A pharmaceutical composition for use in treating or preventing fibrosis in a tissue or an organ, comprising an antibody or an antigen-binding fragment thereof according to any of [1] to [3].

[5] A pharmaceutical composition for use in suppressing the activity of fibroblasts in a tissue or an organ, comprising an antibody or an antigen-binding fragment thereof according to any of [1] to [3].

[6] A pharmaceutical composition for use in accelerating healing of inflammation in an inflammatory tissue, comprising an antibody or an antigen-binding fragment thereof according to any of [1] to [3].

[7] A method for analyzing the presence or absence of inflammation in a tissue, comprising determining the presence of CHL1 protein in the tissue.

[8] The method according to [7], wherein the detection of the presence or absence of the CHL1 protein is performed using an antibody that binds to CHL1 protein, or an antigen-binding fragment thereof.

[9] The method according to [7], wherein the detection of the presence or absence of the CHL1 protein is performed using an antibody or an antigen-binding fragment thereof according to any of [1] to [3].

[10] A diagnostic drug for use in diagnosing the presence or absence of inflammation in a tissue, comprising an antibody that binds to CHL1 protein, or an antigen-binding fragment thereof.

[11] A probe for the detection of fibrosis-inducing non-hemocyte cells, comprising CHL1 protein.

BRIEF DESCRIPTION OF DRAWINGS

FIG. 1 shows the expression of genes having a name indicated on the right side of the drawing.

FIG. 6A shows that the ability to repair enteritis is reduced in a CHL1KO mouse by using the body weight recovery of the DSS-induced enteritis model as an index. FIG. 6B shows a large intestine tissue image obtained by hematoxylin-eosin staining. In FIG. 6B, the delayed reformation of epithelial cells is seen in the CHL1KO mouse. FIG. 6C shows that the degree of fibroblast activation is reduced in the CHL1KO mouse due to the expression of a smooth muscle actin in large intestine fibroblasts so that the recruitment of fibroblasts into epithelial cells is delayed. FIG. 6C shows that the ability to accumulate epithelial cells (stained with EpCAM) and fibroblasts (stained with aSMA) in an inflammatory tissue is reduced in the CHL1KO mouse.

DESCRIPTION OF EMBODIMENTS

Figure 1:
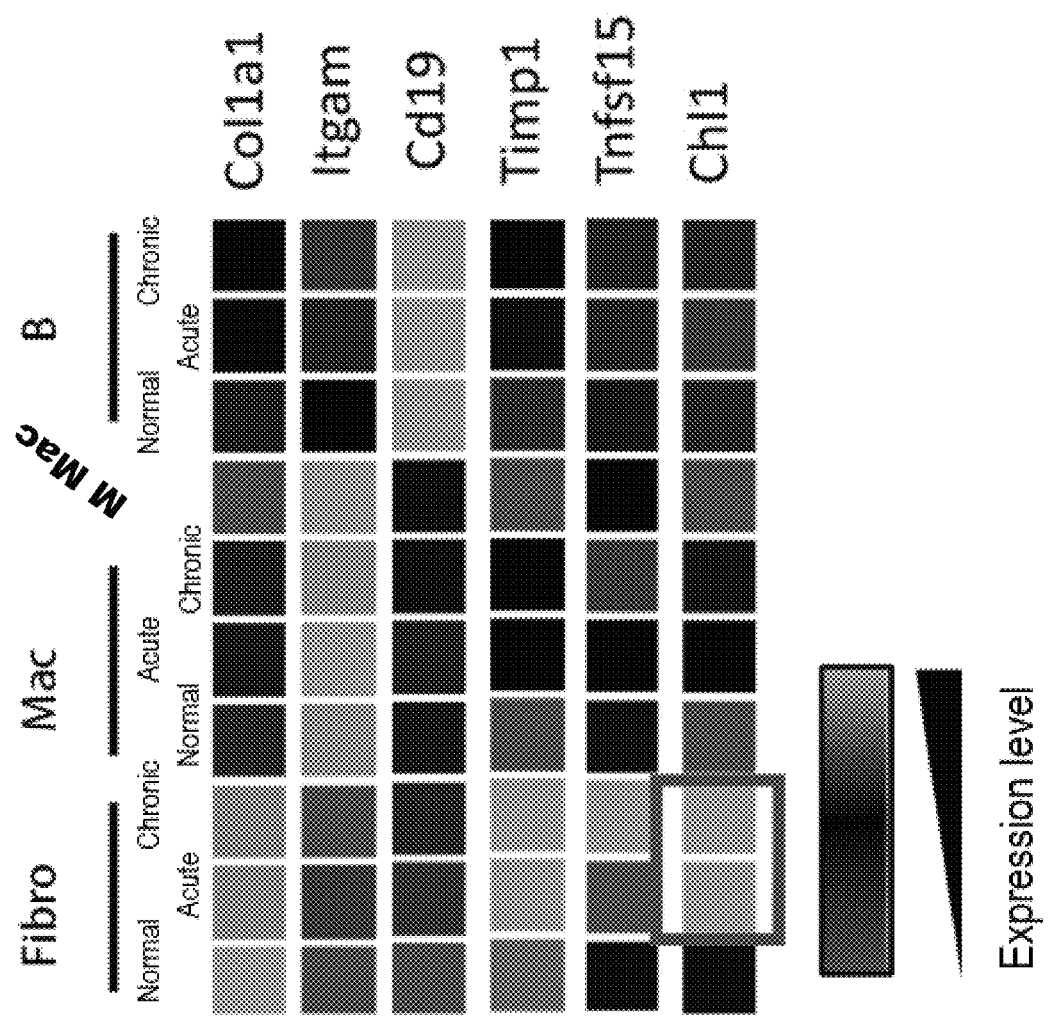
FIG. 1 is a diagram showing results of expression analysis using a microarray. In the drawing, "Fibro" represents a fibroblast, "Mac" represents a macrophage, "BM Mac" represents a bone marrow macrophage, and "B" represents a B cell. In the drawing, "Normal" represents a normal fibroblast, "Acute" represents a fibroblast that induced acute inflammation, and "Chronic" represents a fibroblast that induced chronic inflammation.

In the present specification, the term "subject" may be a mammal and is preferably a human. The subject may be a subject having tissue inflammation or having the risk of developing tissue fibrosis.

In the present specification, the term "inflammation" refers to the protective response of a living tissue to a disorder. Tissues reportedly involved in inflammation are usually terminal vascular beds, blood and connective tissues. A cause is removed by a series of responses for tissue repair. In the present specification, the term "acute inflammation" or "acute phase of inflammation" means inflammation involved in tissue repair, and the term "chronic inflammation" or "chronic phase of inflammation" means inflammation after the tissue repair. In general, the acute inflammation clinically refers to inflammation within approximately 7 days from development of a disorder in a tissue, and the chronic inflammation clinically refers to inflammation that is sustained beyond 7 days (e.g., in months or in years).

In the present specification, the term "fibrosis" means that an excess of collagen is deposited in a tissue due to chronic inflammation so that the tissue is hardened. In the process of fibrosis, fibroblasts are differentiated and matured into myofibroblasts, which then actively produce and secrete collagen. Then, the cells themselves disappear, resulting in fibrotic connective tissues. Since the process of fibrosis is inconspicuous, fibrotic disease may be found after progression of the fibrosis. However, the fibrotic disease is a disease that cannot be treated. Therefore, it is important to prevent the disease.

In the present specification, the term "active fibroblasts" refer to a cell population with the enhanced ability to produce collagen as compared with the steady state, among fibroblasts. Examples thereof include a population containing myofibroblasts. The active fibroblasts are produced from fibroblasts at the acute phase and chronic phase of inflammation.

In the present specification, the term "antibody" means an immunoglobulin and includes a polyclonal antibody and a monoclonal antibody. The antibody is preferably a monoclonal antibody. Examples of the origin of the antibody include, but are not particularly limited to, a nonhuman animal antibody, a nonhuman mammalian antibody, and a human antibody. The antibody may be a chimeric antibody, a humanized antibody, or a human antibody. Also, the antibody may be a bispecific antibody.

The antibody assumes a structure where two heavy chains associate with two light chains. Each heavy chain consists of a heavy chain variable region (VH), a heavy chain constant region (CH1), a hinge region, CH2, and CH3, and each light chain consists of a light chain variable region (VL) and a light chain constant region (CL).

In the present specification, the term "antigen-binding fragment" means a portion of the antibody that maintains binding activity against the antigen. The antigen-binding fragment may comprise the heavy chain variable region or the light chain variable region, or both, of the antibody of the present invention. The antigen-binding fragment may be chimerized or humanized. Examples of the antigen-binding fragment include Fab, Fab', F(ab')$_2$, Fv, scFv (single-chain Fv), diabody, and sc(Fv)$_2$ (single-chain (Fv)$_2$). Such a fragment of the antibody can be obtained, for example, by treating the antibody with an enzyme, though the obtainment of the fragment is not limited thereto. For example, the antibody can be digested with papain to obtain Fab. Alternatively, the antibody can be digested with pepsin to obtain F(ab')₂, which can be further reduced to obtain Fab'. In the present invention, such an antigen-binding fragment of the antibody can be used.

In the present specification, CHL1 is also called cell adhesion molecule L1-like or L1 cell adhesion molecule 2. CHL1 has originally been known as a molecule that is expressed in the brain and is causative of intellectual impairment. CHL1 is considered to function in neuronal synapses.

In the present specification, the term "antibody-drug conjugate" (ADC) means a conjugate of the antibody and a drug. The drug is delivered to a target site through binding to the antibody and is capable of exerting functions at the delivery site. In ADC, the antibody and the drug may be linked via a linker. The design and preparation method of ADC are well known to those skilled in the art.

The present invention provides the following antibody or antigen-binding fragment thereof:

[1] An antibody that binds to CHL1 protein, or an antigen-binding fragment thereof, wherein the antibody or the antigen-binding fragment thereof neutralizes the binding of the CHL1 protein to a fibroblast.

According to the present inventors, an antibody that can neutralize the binding of CHL1 to a fibroblast was able to suppress collagen deposition and fibroblast activation in a tissue at the chronic phase of inflammation. Thus, this antibody or antigen-binding fragment is considered to be able to suppress collagen deposition and fibroblast activation in a tissue at the chronic phase of inflammation by neutralizing the binding of CHL1 to a fibroblast. In one embodiment, this antibody or antigen-binding fragment neutralizes the binding of CHL1 to a non-immune and non-epithelial non-hemocyte cell (in the present specification, this cell is also referred to as a "fibrosis-inducing non-hemocyte cell"), such as a myofibroblast, of the lamina propria and a submucosal layer. Possible receptors of CHL1 are proteins including adhesion molecules such as integrin and vitronectin (Katic J, J Neurosci. 2014 Oct. 29; 34 (44): 14606-23. doi: 10.1523/JNEUROSCI.3280-13.2014), and a serotonin receptor (Kleene R, J Cell Sci. 2015 Dec. 15; 128 (24): 4642-52. doi: 10.1242/jcs.176941).

The present invention also provides

[2] an antibody that binds to CHL1 protein, or an antigen-binding fragment thereof, wherein the antibody is
(1) an antibody having a heavy chain variable region having heavy chain CDR1 having the amino acid sequence set forth in SEQ ID NO: 1, heavy chain CDR2 having the amino acid sequence set forth in SEQ ID NO: 2 and heavy chain CDR3 having the amino acid sequence set forth in SEQ ID NO: 3, and a light chain variable region having light chain CDR1 having the amino acid sequence set forth in SEQ ID NO: 5, light chain CDR2 having the amino acid sequence set forth in SEQ ID NO: 6 and light chain CDR3 having the amino acid sequence set forth in SEQ ID NO: 7, or
(2) an antibody that competes with the antibody (1) for binding to the CHL1 protein.

The present invention also provides

[3] the antibody or the antigen-binding fragment thereof according to [2], wherein the antibody is (3) an antibody having a heavy chain variable region having the amino acid sequence set forth in SEQ ID NO: 4 and a light chain variable region having the amino acid sequence set forth in SEQ ID NO: 8, or (4) an antibody that competes with the antibody (3) for binding to the CHL1 protein.

The antibody (1) or (3) can neutralize the binding of CHL1 to a non-immune and non-epithelial non-hemocyte cell, such as a myofibroblast, of the lamina propria and a submucosal layer. This is probably because the antibody binds to the surface, to which the CHL1 protein binds, of the non-immune and non-epithelial non-hemocyte cell, such as a myofibroblast, of the lamina propria and a submucosal layer, and causes steric hindrance ascribable to the antibody so that the CHL1 protein can no longer bind to the fibroblast. Thus, the antibody that competes with the antibody (1) or (3) can also bind to the surface, to which the CHL1 protein binds, of the non-immune and non-epithelial non-hemocyte cell such as a myofibroblast, and cause steric hindrance, thereby neutralizing the binding of CHL1 to the non-immune and non-epithelial non-hemocyte cell such as a myofibroblast. If necessary, whether or not to neutralize the binding of CHL1 to the non-immune and non-epithelial non-hemocyte cell such as a myofibroblast may be confirmed.

The present invention provides an antibody that competes with the antibody (1) or (3) for binding to the CHL1 protein, wherein the antibody is capable of neutralizing the binding of CHL1 to a non-immune and non-epithelial non-hemocyte cell such as a myofibroblast.

The antibody of the present invention can reduce the activity of fibroblasts, reduce collagen production, or suppress collagen deposition, in a tissue or an organ (particularly, a region characterized by inflammation in a tissue or an organ inducing inflammation). The antibody of the present invention can thereby prevent tissue or organ fibrosis in the tissue or the organ (particularly, a region characterized by inflammation in a tissue or an organ inducing inflammation). Thus, the present invention provides a composition or a pharmaceutical composition for use in reducing the activity of fibroblasts, reducing collagen production, or suppressing collagen deposition, comprising the antibody of the present invention. The present invention also provides a pharmaceutical composition for use in treating fibrotic disease, comprising the antibody of the present invention. The present invention also provides a pharmaceutical composition for use in preventing tissue fibrosis in a tissue where inflammation has occurred, comprising the antibody of the present invention. Examples of the tissue or the organ where inflammation has occurred include the intestines (e.g., the small intestine and the large intestine). The pharmaceutical composition of the present invention is capable of preventing tissue fibrosis in a tissue where chronic inflammation has occurred. Thus, the pharmaceutical composition of the present invention may be used for a tissue where chronic inflammation has occurred, particularly, a tissue where chronic inflammation has occurred before completion of tissue fibrosis. Thus, in one embodiment, the pharmaceutical composition of the present invention can be administered to a subject having chronic inflammation (particularly, a subject having chronic inflammation before completion of tissue fibrosis). The pharmaceutical composition of the present invention may be used for preventing tissue or organ fibrosis in a tissue or an organ before occurrence of inflammation (i.e., a tissue or an organ in the steady state). In the present specification, the term "treatment" includes slowing of aggravation of symptoms, stopping of aggravation of symptoms, and improvement in symptom. In the present specification, a portion of the "organ" is also referred to as a "tissue".

In one embodiment, the pharmaceutical composition of the present invention can be administered to a subject having an inflammatory disease selected from inflammatory bowel diseases such as Crohn disease and ulcerative colitis.

As mentioned later, in a subject having inflammation, CHL1 is released into a tissue, into a body fluid or into excrement. Thus, the pharmaceutical composition of the present invention may be administered to a CHL1-positive subject.

A pharmaceutical composition or a medicament comprising the antibody of the present invention as an active ingredient can be formulated by a pharmaceutical method known in the art. For example, the pharmaceutical composition or the medicament of the present invention may comprise a pharmaceutically acceptable excipient. The excipient can be an excipient that may be appropriately administered for providing an effective amount of the antibody of the present invention serving as an active ingredient to a subject. In one embodiment, the pharmaceutical composition or the medicament of the present invention can be an injection. The injectable excipient can be a sterile aqueous solution, for example, a pharmaceutically acceptable buffer solution such as a Ringer's solution, a Hank's solution or saline, or an isotonic solution containing glucose or any of other aids. Examples of the aid include alcohols such as ethanol, polyalcohols such as polyethylene glycol, and nonionic surfactants such as polysorbate 80. The aid can be added for formulation. Sesame oil, coconut oil or soybean oil can be used as an injectable oily liquid, and benzyl benzoate or benzyl alcohol can be used as an aid. The pharmaceutical composition or the medicament of the present invention can be administered parenterally (e.g., intravenously or intraperitoneally) in the form of an injection.

Preparation of Antibody

The antibody can be prepared by a method well known to those skilled in the art. Specifically, the polyclonal antibody can be obtained by immunizing animals with the antigen and an adjuvant, and obtaining the plasma of the immunized animals. Alternatively, the antibody may be obtained by immunizing animals with the antigen and an adjuvant, obtaining B lymphocytes from the immunized animals, fusing the B lymphocytes with myeloma cells to form hybridomas, and cloning a hybridoma producing the desired antibody. In the immunization step, a cell line (e.g., 293 cells or CHO cells) is forced to express the antigen, and animals may be immunized with the resulting cells. Since the CHL1 protein expressed in the cell line is exposed to cell surface, the immunized animals are capable of producing an antibody to the CHL1 protein. Alternatively, cells expressing the CHL1 protein, preferably the CHL1 protein, may be purified and used in the immunization of animals.

The chimeric antibody can be prepared by a method well known in the art. The chimeric antibody can be prepared, for example, by replacing the constant regions of an antibody with the constant regions of a human antibody. The humanized antibody comprises, for example, nonhuman animal-derived complementarity-determining regions (CDRs), human antibody-derived framework regions and human antibody-derived constant regions. The humanized antibody can be obtained, for example, by grafting the CDRs to a human antibody. The human antibody can be obtained, for example, by immunizing human antibody-producing genetically modified mice with the antigen. The bispecific antibody is an antibody that can bind to two different epitopes or antigens, and can be prepared by a method well known to those skilled in the art. The bispecific antibody can be prepared, for example, by a method of further fusing cells producing two different antibodies to prepare hybrid hybridomas, or by expressing a $V_H$ region and a $V_L$ region on one polypeptide chain via a linker that is too short to form a pair between these two regions, and forming a complex with another polypeptide chain having a $V_H$ region and a $V_L$ region complementary to the $V_H$ region and the $V_L$ region to be paired therewith.

The antibody that competes with a certain antibody for binding to the antigen can be confirmed by competition assay well known to those skilled in the art. In the competition assay, an antibody that can block the binding of the desired antibody, for example, by at least 20%, preferably at least 20 to 50%, more preferably at least 50%, can be regarded as an antibody that competes therewith for binding to the same antigen. The competing antibody can be confirmed by cross-blocking assay, preferably competitive ELISA assay. In the cross-blocking assay, for example, a microtiter plate is coated with the antigen, and a candidate competing antibody is added to the plate, followed by incubation to form the binding between the antigen and the candidate antibody. Then, the desired antibody is labeled and then further added to each well. The plate is incubated and washed, and the amount of the desired antibody bound can be quantified to determine whether or not the antibody has competed. When the candidate antibody competes therewith, the amount of the label remaining in the well should be decreased.

The antibody that can neutralize the binding of the CHL1 protein to a fibroblast can be confirmed on the basis of whether or not the antibody competes with CHL1 for binding to a non-immune and non-epithelial non-hemocyte cell such as a myofibroblast. For example, as described in Examples mentioned later, when a fusion protein of the CHL1 protein bound with a tag (e.g., an Fc tag) is allowed to bind to a non-immune and non-epithelial non-hemocyte cell such as a myofibroblast, the binding of the CHL1 protein to the cell can be detected using an antibody that binds to the tag. An antibody that can block this binding (binding of CHL1 to the non-immune and non-epithelial non-hemocyte cell such as a myofibroblast), for example, by at least 20%, preferably at least 20 to 50%, more preferably at least 50%, can be regarded as an antibody that can neutralize the binding of the CHL1 protein to the non-immune and non-epithelial non-hemocyte cell as a myofibroblast.

In another aspect, the present invention provides a method for analyzing (or testing) the presence or absence of inflammation in a tissue, comprising determining the presence (presence or absence) of CHL1 protein in the tissue. According to the present inventors, the CHL1 protein exhibited high expression in an inflammatory tissue. According to the present inventors, the CHL1 protein was secreted from a tissue having inflammation and was able to be detected in the body fluid, particularly, excrement, of an individual. Thus, the determination of the presence or absence of the CHL1 protein in the tissue includes the determination of the presence of the CHL1 protein in an inflammatory tissue as well as the determination of the presence of the CHL1 protein in a body fluid or excrement, secreted from the inflammatory tissue.

In one embodiment of the present invention, the presence of the CHL1 protein can be detected using an antibody that binds to CHL1. In one embodiment, the antibody may be the antibody of the present invention. In another embodiment, the presence of the CHL1 protein can be determined by measuring the mRNA level of CHL1. The mRNA level can be measured by a method well known to those skilled in the art, such as Southern blotting or quantitative PCR.

In one aspect, the present invention provides a diagnostic drug or a diagnostic kit for use in diagnosing the presence or absence of inflammation in a tissue, comprising an antibody that binds to CHL1 protein, or an antigen-binding fragment thereof. The diagnostic kit may further have an additional configuration in addition to the diagnostic drug, and may have a manual that explains a method for diagnosing inflammation. In one aspect, the present invention provides a testing drug or a testing kit for use in diagnosing the presence or absence of inflammation in a tissue, comprising an antibody that binds to CHL1 protein, or an antigen-binding fragment thereof. The testing kit may further have an additional configuration in addition to the testing drug, and may have a manual that explains a method for testing inflammation.

In one aspect of the present invention, the CHL1 protein binds to a non-immune and non-epithelial non-hemocyte cell such as a myofibroblast. Thus, the CHL1 protein can be used in the detection of myofibroblasts. For example, upon contact of the CHL1 protein bound with or without a tag with a cell fraction containing myofibroblasts, the CHL1 protein binds to a myofibroblast. The myofibroblasts can be detected by detecting the cell bound on its surface with the CHL1 protein by flow cytometry. Also, the myofibroblasts can be enriched or isolated by gating the cell bound on its surface with the CHL1 protein by flow cytometry. Thus, in one aspect, the present invention provides a probe for the detection of fibrosis-inducing non-hemocyte cells such as myofibroblasts, comprising CHL1 protein. In one embodiment, the present invention provides a composition for use in enriching or isolating myofibroblasts, comprising CHL1 protein. In this context, the "enrichment" means the elevation of the ratio of fibrosis-inducing non-hemocyte cells such as myofibroblasts to all cells, and the "isolation" means the substantial isolation of fibrosis-inducing non-hemocyte cells such as myofibroblasts from other cells. The present invention also provides a cell population comprising fibrosis-inducing non-hemocyte cells thus enriched or isolated using the probe for detection. The cell population comprising fibrosis-inducing non-hemocyte cells enriched or isolated using the probe for detection can be used in, for example, the detection of the neutralization of the interaction between CHL1 and a non-immune and non-epithelial non-hemocyte cell of the lamina propria and a submucosal layer by an antibody or the like.

In one aspect, the present invention provides a method for preventing fibrosis in an inflammatory tissue in a subject in need thereof, comprising administering the antibody of the present invention to the subject. In one aspect, the present invention provides a method for diagnosing the presence or absence of an inflammatory tissue in a subject having the inflammatory tissue or a subject having the possibility of having the inflammatory tissue, comprising determining the presence of CHL1 protein in the tissue. In one aspect, the present invention provides a method for enriching or isolating myofibroblasts, comprising: contacting a probe comprising CHL1 protein with a cell fraction containing myofibroblasts; and separating cells bound with the CHL1 protein from unbound cells.

In one aspect, the present invention provides use of the antibody of the present invention in the manufacture of a composition or a medicament for use in reducing the activity of fibroblasts, reducing collagen production, or suppressing collagen deposition. In one aspect, the present invention provides use of the antibody of the present invention in the manufacture of a medicament for use in suppressing the activity of fibroblasts in an inflammatory tissue. In one aspect, the present invention provides use of an antibody that binds to CHL1 protein in the manufacture of a diagnostic drug or a diagnostic kit for use in diagnosing the presence or absence of inflammation in a tissue.

EXAMPLES

Example 1: Microarray analysis in activated fibroblast

This Example is aimed at identifying a factor, gene expression of which varies in activated fibroblasts.

(A) COL1a2-GFP tg/+C57Bl/6 mice (kindly provided by prof. Inagaki, Tokai University School of Medicine) were used. Untreated normal mice (in the drawings, also abbreviated to "Normal"), mice on days 7 to 10 after free drinking of 2.25 to 2.5% aqueous dextran sodium sulfate solution (Medical & Biological Laboratories Co., Ltd. MBL) (5 days) (in the drawings, also abbreviated to "Acute"), and mice on days 70 to 90 after 3 repetitions of acute enteritis at 2-week intervals (in the drawings, also abbreviated to "Chronic") were dissected, and their lamina propria cells of the large intestine were isolated by treatment with ethylenediaminetetraacetic acid and collagenase. The obtained cells were stained with antibodies and sorted using a cell sorter (FACS Aria III Becton, Dickinson and Company (BD)).

Fibroblasts (COL1a2-GFP-positive CD45-negative podoplanin-positive), macrophages (CD45-positive F480-positive CD11b-positive), B cells (CD45-positive CD19-positive B220-positive), and C57Bl/6 mouse-derived bone marrow macrophages (BM Mac) induced from Recombinant Mouse M-CSF (carrier-free) (BioLegend, Inc.: 576404) were fractionated by a routine method.

The antibodies used in this Example were as follows.

TABLE 1

| Distributor | Antibody name | Product No. |
|---|---|---|
| BioLegend | DyLIght 649 Donkey anti-rabbit IgG | 406406 |
| CSTjapan | Vimentin XR rabbit mAb (Alexa Fluor ® 647 conjugate) | 9856S |
| BioLegend | Alexa Fluoro 647 anti-mouse CD326(EpCAM) | 118211 |
| Life Technologies | Goat anti human IgG(H + L) secondary antibody, Alexa 647 conjugate | A21445 |
| Biolegend | APC goat anti-Rat IgG | 405407 |
| ebioscience | F(ab) anti-mouse IgGeFluor660 | 50-4010 |
| BD | APG rat anti-mouse Ly6c | 560595 |
| Biolegend | APC anti-mouse podoplanin | 127410 |
| Biolegend | APC anti-mouse F4/80 | 123115 |
| Biolegend | FITC anti mouse IgG2a | 407105 |
| Biolegend | FITC anti-mouse Ly-6C | 128006 |
| BD | FITC-Rat anti-mouse CD103 | 557494 |
| Biolegend | PE anti-mouse podoplanin | 127407 |
| Biolegend | PE anti-mouse F480 | 123110 |
| Sigma | Anti-Actin, α-Smooth Muscle - Cy3 ™ antibody, Mouse monoclonal clone 1A4, purified from hybridoma cell culture | C6198-100UL |
| Biolegend | PE anti-mouse sca1 | 108107 |
| Biolegend | PE anti-mouse CD146 | 134703 |
| BioLegend | PECy7 anti-mouse CD146 | 134714 |
| BD | PECy7 rat anti-mouse CD45 | 552848 |
| Biolegend | APC/Cy7 anti-mouse F480 | 123118 |
| Biolegend | APC/Cy7 anti-mouse CD45 | 103115 |
| Biolegend | APC/Cy7 anti-mouse CD4 | 100414 |
| Biolegend | Pacific Blue anti-mouse CD19 | 115523 |
| Biolegend | Pacific Blue Anti-mouse CD11b antibody | 101224 |
| Biolegend | Pacific Blue Anti-mouse CD45 antibody | 103126 |
| Biolegend | Pacific Blue anti-mouse CD90, 2 | 105324 |

Then, RNA was purified using TRIZOL (Thermo Fisher Scientific Inc.) and SuperScript VILO (Thermo Fisher Scientific Inc.). The obtained RNA was analyzed using Agilent gene expression microarray according to the manufacturer's manual attached to the product. The reagents used in the microarray were as follows.

TABLE 2

| Agilent product No. | Product name |
|---|---|
| G4852A | SurePrint G3 Mouse GE microarray kit 8 × 60K |
| 5190-2305 | Low Input Quick Amp Labeling Kit (1 color) |
| 5188-5242 | Gene Expression Hybridization kit |
| 5188-5282 | RNA Spick In Kit (1 color) |
| 5188-5327 | Gene Expression Wash pack |
| G2534-60014 | 8 × 60K Gasket slide for 8 × 60K array format |

The results were as shown in FIG. 1. As shown in FIG. 1, Chl1 was able to be identified as a factor strongly expressed only in fibroblasts at the acute phase and chronic phase of induced inflammation.

Example 2: Verification of Tissue-Specific Expression of Chl1

Next, the expression of Chl1 was confirmed using various tissues or cells.

(B) The intestinal epithelium (EpCAM-positive CD45-negative), fibroblasts (COL1a2-GFP-positive CD45-negative podoplanin-positive), macrophages (F480-positive CD11b-positive), CD4-positive T cells, B cells (CD19-positive B220-positive), and lamina propria cells of the large intestine (whole colon cells) were isolated in the same way as above. RNA was purified from each cell using TRIZOL (Thermo Fisher Scientific Inc./Invitrogen: 15596018) and subsequently reverse-transcribed using VILO (Thermo Fisher Scientific Inc./Invitrogen: 11755500). The expression analysis of Chl1 was conducted using Universal Probe Library (Roche Life Science) and LightCycler™ 480 system (Roche Life Science). Comparison with the expression of Gapdh is shown (n=3). The results were as shown in FIG. 2.

Figure 2:
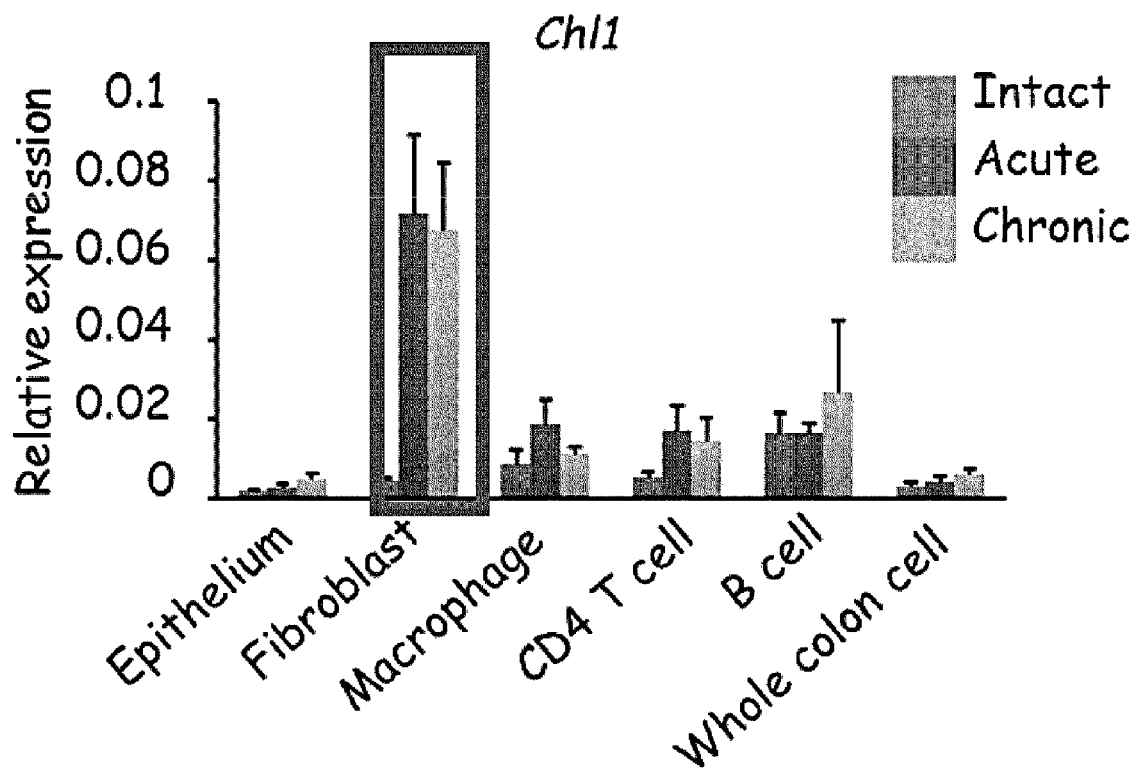
FIG. 2 is a diagram showing the expression level of Chl1 gene in various cells.

As shown in FIG. 2, Chl1 exhibited high expression in fibroblasts, particularly, fibroblasts at the acute phase ("Acute") and chronic phase "Chronic" of induced inflammation. This suggested that Chl1 may be preferably used as a marker for acute and chronic inflammation.

Example 3: Identification of Expression Site of Chl1

This Example showed that Chl1 is expressed on a cell membrane.

(C) Lamina propria cells of the large intestine were isolated from normal (day 0) wild-type C57Bl/6 mice and CHL1-knockout mice (kindly provided by D. Montag Leibniz, Institute for Neurobiology, German), and C57Bl/6 mice at the acute phase (days 10 to 15) of inflammation induced by an aqueous dextran sodium sulfate solution, and analyzed for CHL1 expression by flow cytometry analysis (FACSCalibur (BD)) using Anti-Mouse CHL-1/L1CAM-2 Monoclonal Antibody (R&D Systems, Inc.) and APC goat anti-rat IgG (BioLegend, Inc.: 405407). The expression of CHL1 on podoplanin-positive fibroblasts was shown. The results were as shown in FIG. 3.

Figure 3:
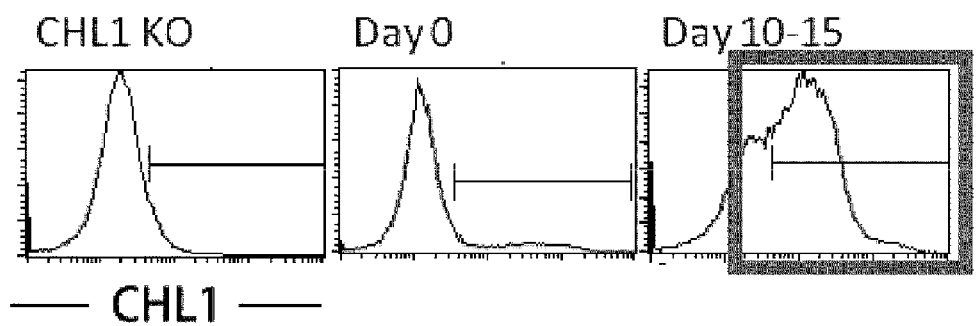
FIG. 3 is a diagram showing that CHL1 is expressed on a cell membrane at the time of inflammation.

As shown in FIG. 3, the expression of CHL1 on cell surface was confirmed at the acute phase (days 10 to 15) as compared with the results of flow cytometry analysis on the normal (day 0) and CHL1-knockout (KO) mice. This demonstrated that Chl1 is expressed on a cell membrane at the time of inflammation.

(D) Next, the expression of Chl1 was confirmed using a mouse large intestine tissue in which chronic inflammation was induced, and a human Crohn disease large intestine sample.

The large intestine was collected from each of normal COL1a2-GFP tg/+C57Bl/6 mice and COL1a2-GFP tg/+ C57Bl/6 mice having chronic enteritis, and then fixed in 4% PFA, which was subsequently replaced with 10% or 20% sucrose. Frozen tissues were prepared from the obtained tissues using an embedding medium for frozen tissue section preparation (Tissue-Tek O.C.T. Compound). Sliced sections were prepared from the frozen tissues, stained with Anti-Mouse CHL-1/L1CAM-2 Monoclonal Antibody (R&D Systems, Inc.), Goat anti human IgG (H+L) secondary antibody, Alexa 647 conjugate (Life Technologies Corp.: A21445), and DAPI (nucleus), and observed under a fluorescence microscope (Keyence Corp.).

The human Crohn disease large intestine sample and a sample of a healthy human subject (kindly provided by Hideki Iizima, Osaka University, Graduate School of Medicine, Department of Gastroenterology and Hepatology) were subjected to the experiment according to the following protocol.

Figure 4:
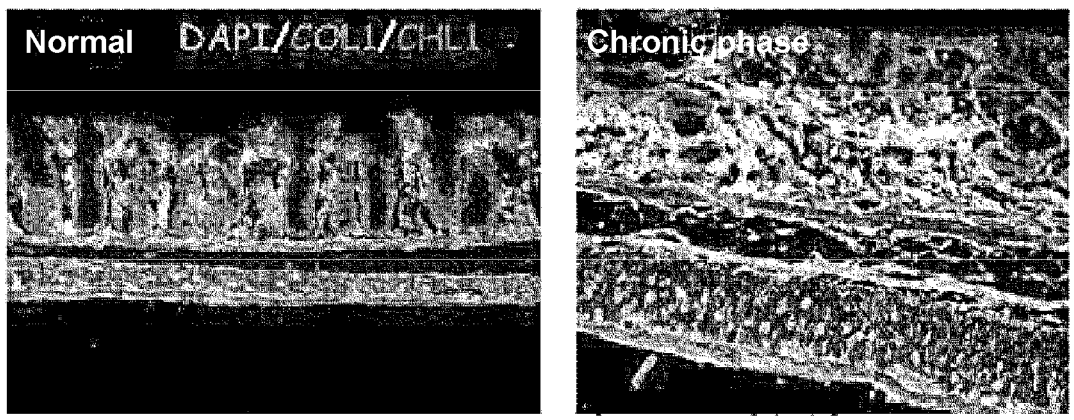
FIG. 4 is a diagram showing the expression of the CHL1 protein at the chronic phase of inflammation and the expression of the CHL1 protein in a human Crohn disease large intestine sample.
Figure 4:
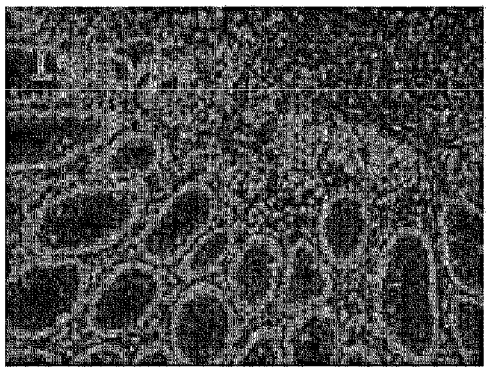
Figure 4:
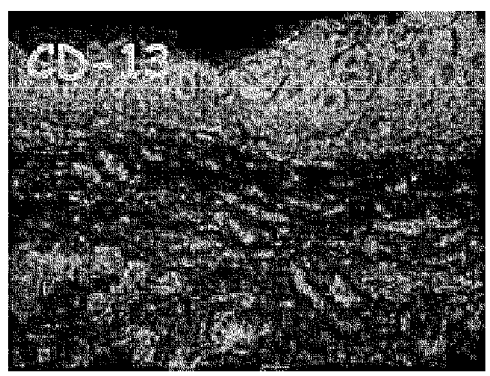
Figure 4:
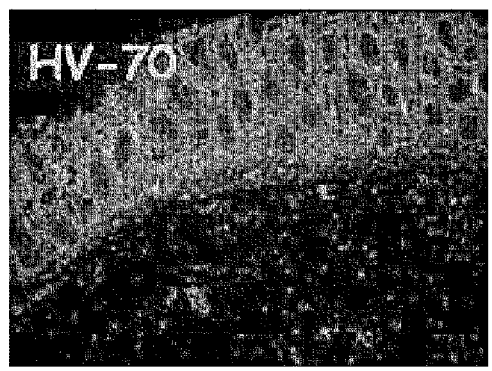
Figure 4:
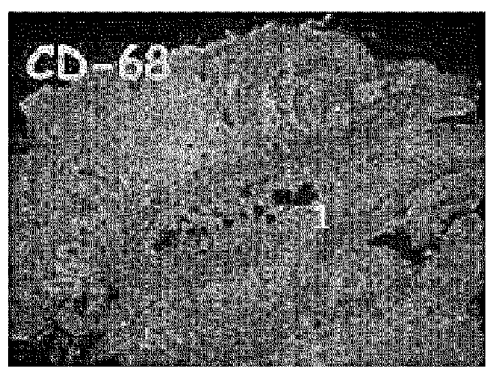

1. Activation using Retrievagen A (BD: 550524)
2. Blocking with Anti-human Fc block (ebio 14-9161-73 mouse IgG2a) (room temperature, 30 min)
3. Overnight incubation with anti-human CHL1 rabbit polyclonal antibody (Abcam PLC: ab106269) as a primary antibody (low-temperature room), 100 uL/slides
4. Washing for 5 minutes 2 times using PBS under gentle shaking conditions
5. Overnight incubation with anti-rabbit Alexa 594 donkey antibody (BioLegend, Inc.: 406405) as a secondary antibody (low-temperature room), 100 uL/slides
6. Washing for 5 minutes 2 times using PBS under gentle shaking conditions
7. Staining with DAPI (room temperature, 20 min, 100 uL/slides)
8. Washing for 5 minutes 2 times using PBS under gentle shaking conditions
9. Mounting with Fluoromount The results were as shown in FIG. 4. As shown in the upper panels of FIG. 4, at the chronic phase (upper right panel of FIG. 4), the CHL1 molecule was strongly expressed in type I collagen-producing cells (Col1) present in the lamina propria and a submucosal layer. On the other hand, the expression of the CHL1 molecule was hardly observed in the normal tissue (upper left panel of FIG. 4).

Next, immune response in the inflammation sample was confirmed. The results were as shown in the lower panels of FIG. 4. As shown in the lower panels of FIG. 4, the expression of the CHL1 protein was confirmed in the human Crohn disease large intestine sample (Crohn disease sample Nos. CD-13 and CD-68). On the other hand, the expression was unable to be observed in the healthy human subject (HV-70). From these results, the accumulation of the CHL1 protein throughout the tissue was able to be confirmed in the Crohn disease large intestine sample.

Example 4: Role of CHL1 in Repair of Damaged Muscle Fiber

In this Example, the physiological functions of CHL1 were examined.

Lamina propria cells of the large intestine were isolated from each of wild-type (WT) and CHL1 KO mice having acute enteritis by the method described above, and cultured in a medium having the composition shown in the table below, and adherent cells were collected to obtain large intestine subepithelial myofibroblasts.

TABLE 3

| | Manufacturer | Concentration |
|---|---|---|
| GlutaMAX™ Supplement | GIBCO | ×1 |
| Recombinant Murine EGF | Peprotech | 20 ng/ml |
| apo-Transferrin from Human | Nacalai Tesque | 10 µg/ml |
| Insulin from bovine pancreas | Sigma | 0.25 U/ml |

The large intestine subepithelial myofibroblasts derived from each of the WT and CHL1 KO mice were inoculated to a 6 cm dish, followed by scratch assay of damaging the cells using the tip of a 100 µL pipette. The manner of recovery of the cells was observed before the start, 14 hours later, and 19 hours later. The results were as shown in FIG. 5.

Figure 5:
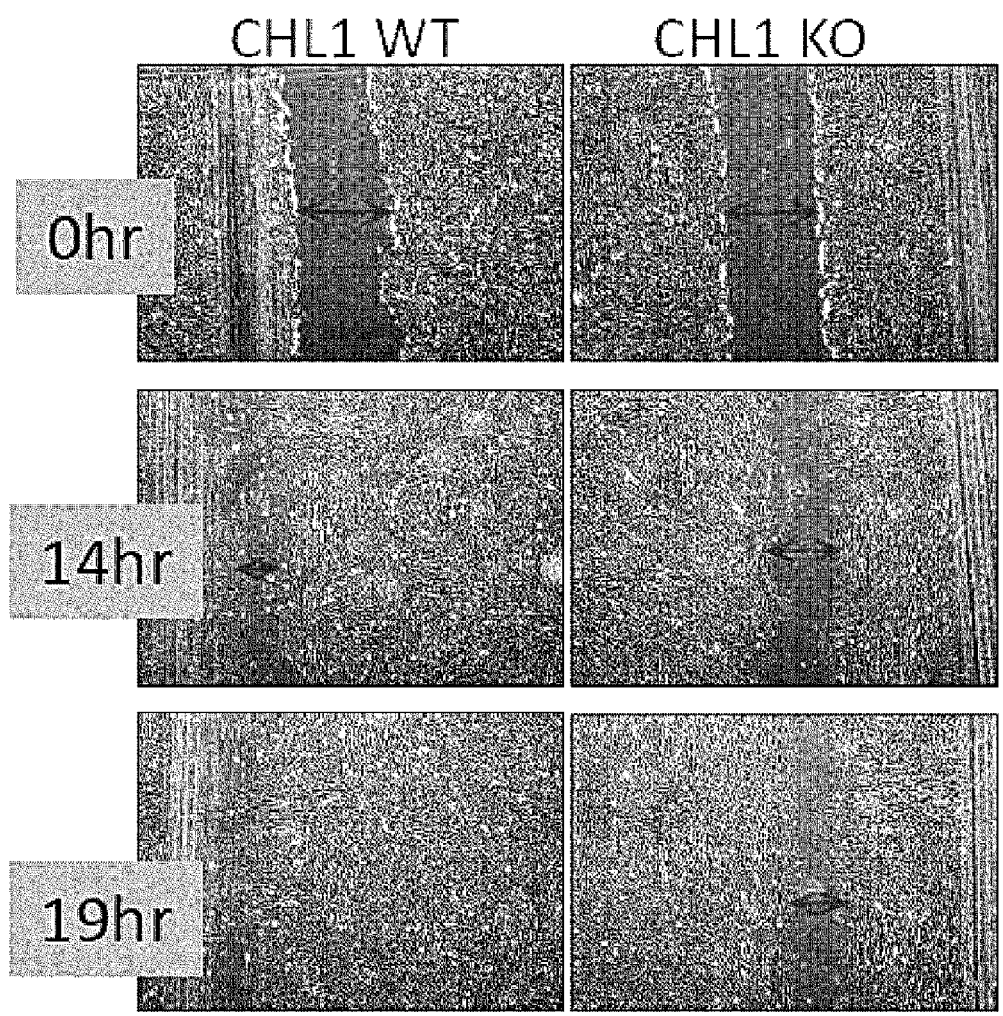
FIG. 5 is a diagram showing the influence of CHL1-knockout (CHL1K0) mouse-derived fibroblasts on the repair of tissue damage.

As shown in FIG. 5, the recovery of the damage site was already confirmed in the WT mouse 14 hours later, whereas the knockout of CHL1 was found to drastically delay the recovery. This indicated that CHL1-knockout fibroblasts have reduced activity.

The role of CHL1 was further analyzed using an enteritis model prepared by the administration of dextran sodium sulfate. Specifically, an aqueous dextran sodium sulfate solution (2.25%) was administered by drinking to wild-type C57Bl/6 mice (n=4) and CHL1 KO mice (n=6) for 5 days. Then, their body weights were measured. On day 18, the large intestine was harvested from each mouse, and fixed in PFA. Then, paraffin sections were prepared and stained with hematoxylin-eosin. CHL WT and CHL KO mice of COL1a2-GFP background were prepared and treated with an aqueous dextran sodium sulfate solution. Then, their large intestine tissues were stained with an anti-EpCAM antibody, an anti-actin antibody, and monoclonal anti-α-smooth muscle actin antibody-Cy3™ labeled (Sigma-Aldrich Co. LLC, C6198-100UL) and observed. The results were as shown in FIGS. 6A-6C.

Figure 6A:
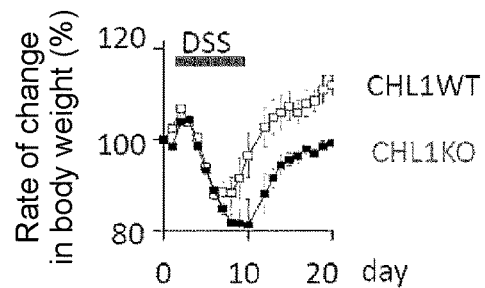
FIGS. 6A-6C are diagrams showing the role of CHL1 in a dextran sodium sulfate (DSS)-induced enteritis model.
Figure 6B:
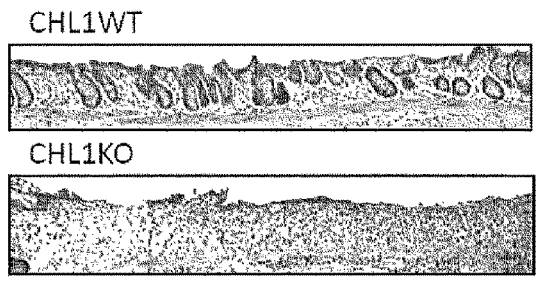
Figure 6C:
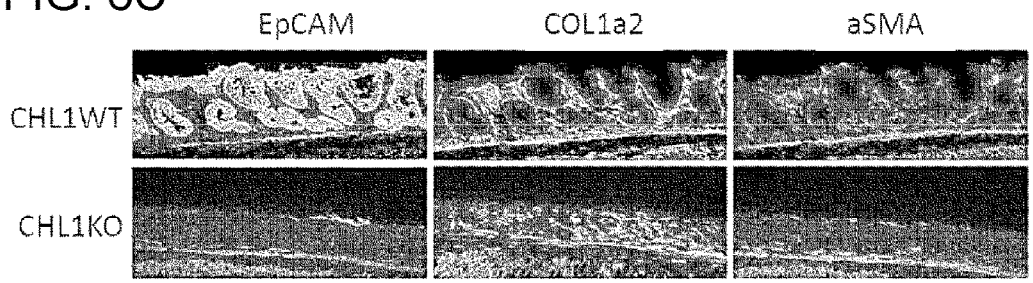

As shown in FIGS. 6A-6C, the reduced activity of large intestine fibroblasts and the delayed healing of the mucosa were observed in the knockout mouse congenitally deficient in CHL1 (FIGS. 6B and 6C). Also, body weight recovery was delayed in the CHL1-deficient knockout mouse as compared with the wild type (FIG. 6A). FIG. 6C shows that the accumulation levels of epithelial cells (stained with EpCAM) and fibroblasts (stained with aSMA) in tissues are lowered. This result is data supporting the delay of tissue repair due to the reduced activity of fibroblasts.

Figure 7:
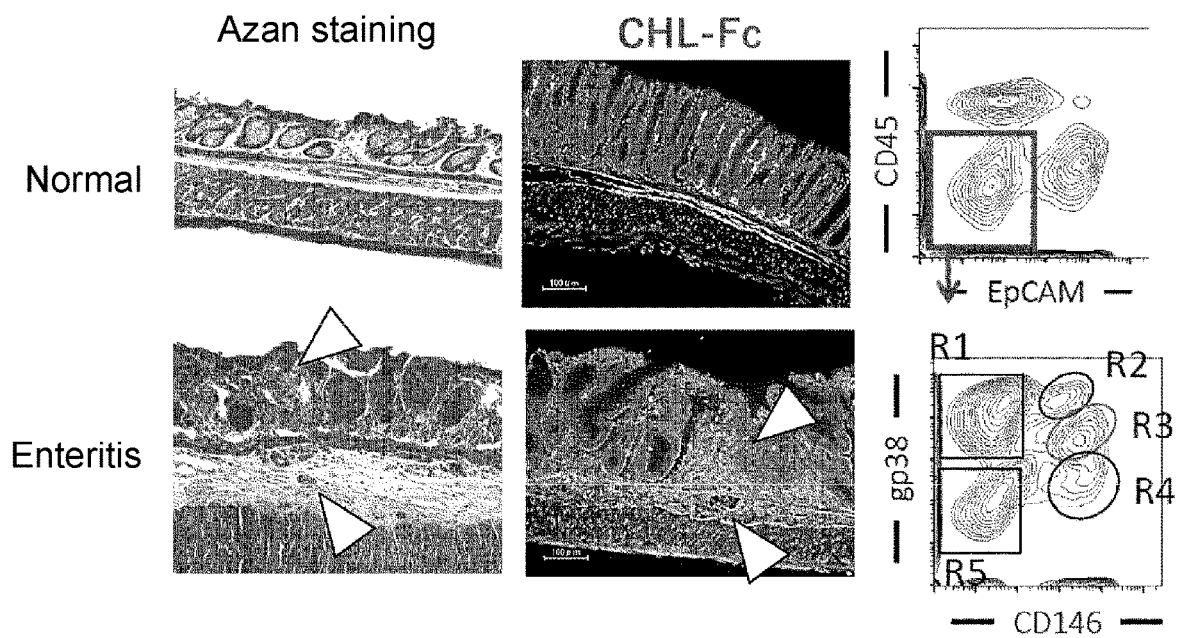
FIG. 7 shows a photograph showing the localization (red; light gray in the drawing) of cells that associate with the CHL1 protein at a fibrosis site (blue site of Azan staining; dark gray in the drawing) of the lamina propria or a submucosal tissue (FIG. 7, left) and the fractions of cells (FIG. 7, right). In the drawing, the arrowheads depict areas with marked fibrosis, which are consistent with the localization of the cell population that associates with the CHL1 protein.

Furthermore, frozen large intestine tissues of normal COL1a2-GFP tg/+ C57Bl/6 mice or COL1a2-GFP tg/+ C57Bl/6 mice having enteritis were stained with mouse CHL-1 protein (Fc tag) (Sino Biological Inc)-goat anti-human IgG (H+L) secondary antibody, Alexa 647 labeled (Life Technologies Corp.: A21445) (red), and DAPI (nucleus), and observed under a fluorescence microscope (Keyence Corp.). The results were as shown in the photographs of the left panels of FIG. 7. As shown in FIG. 7, CHL1 associated with an intestinal subepithelial myofibroblast and a cell localized in a submucosal tissue where fibrosis would occur, in the intestinal tissue in which enteritis was induced (left photographs of FIG. 7).

CD45-negative EpCAM-negative (i.e., fractions that were neither epithelial cells nor immunocytes) lamina propria cells of the large intestine were isolated from normal C57Bl/6 mice, stained with antibodies to podoplanin (gp38) and CD146 (BioLegend, Inc.), and gated into R1, R2, R3, R4, and R5 (see the right panels of FIG. 7). Each of the fractions R1 to R5 was analyzed by FACS using CHL-1 protein (Fc tag) (Sino Biological Inc)-goat anti-human IgG (H+L) secondary antibody Alexa 647 labeled (Life Technologies Corp.: A21445). The results were as shown in FIG. 8.

Figure 8:
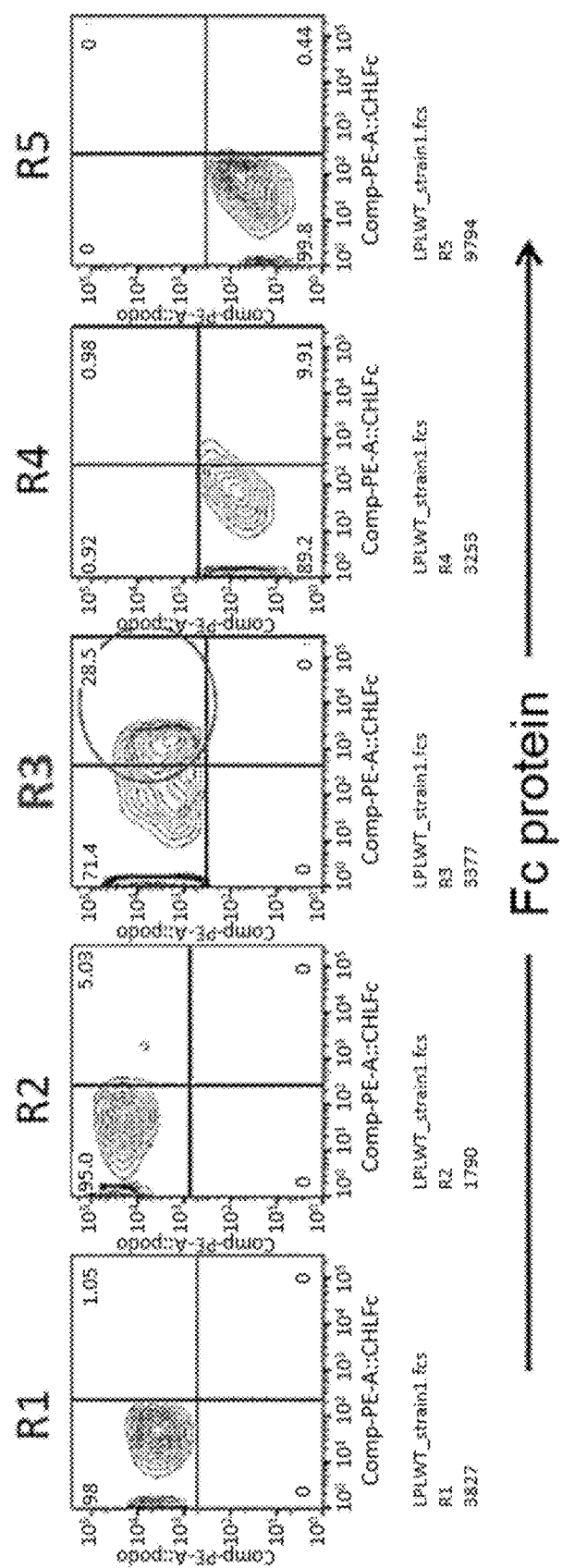
FIG. 8 is a diagram showing that CHL1 binds to some cells of the fraction R3. CHL1 had an Fc tag, and the Fc tag was detected in the drawing.

As shown in FIG. 8, as a result of further gating the CD45-negative EpCAM-negative fractions into R1 to R5 on the basis of gp38 and CD146, and reacting the CHL1 protein with each of the fractions, a cell group associating with CHL1 was confirmed in the fraction R3. The fraction R3 is known as a fraction of myofibroblasts. This suggested that CHL1 functions on myofibroblasts.

Figure 9:
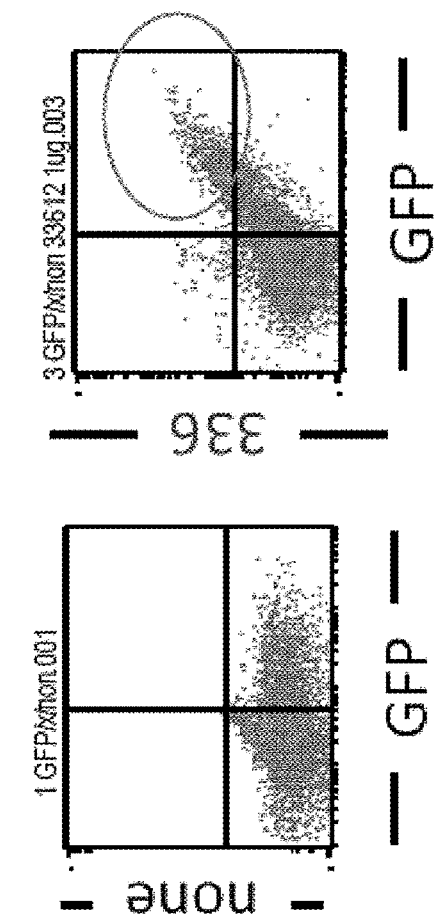
FIG. 9 is a diagram showing that a 336 antibody, a monoclonal antibody to the CHL1 protein, recognizes the CHL1 protein expressed on cell surface.

Example 5: Preparation of Anti-CHL1 Monoclonal Antibody and Functional Analysis of Obtained Antibody Mouse CHL1 gene (mChl1) was cloned into pIRES2-EGFP vector by PCR using Phusion (Thermo Fisher Scientific Inc.: F530L). Y3Ag cells (rat macrophage cell line) were transfected with mChl1 pIRES2-EGFP by electroporation, and four 7-week-old female or male SD rats (CLEA Japan, Inc.) were immunized from their footpads and tail roots with a mixture of the cells with TiterMax Gold (Funakoshi Co., Ltd.: G-1X5). After 3 to 8 immunizations, inguinal lymph nodes or iliac lymph nodes were isolated, and their cells were fused with AG8 myeloma cells using PEG1500 (Roche: 10783641001). The obtained hybridomas were screened in HAT medium (DS Pharma Biomedical Co., Ltd.: 16-808-49) or HT medium (DS Pharma Biomedical Co., Ltd.: 16-809-49) under conditions supplemented with BM condimed H1 (Roche: 11088947001). The culture supernatants were collected and reacted with HEK293 cells transfected with mChl1 pIRES2-EGFP. Then, antibody titers in the supernatants were studied by FACS analysis using APC goat anti-Rat IgG (BioLegend, Inc.: 405407). As shown in FIG. 9, the obtained antibody recognized the CHL1 protein on cell surface.

The hybridoma clone 336 obtained as described above was intraperitoneally administered at approximately $5 \times 10^6$ cells to a Balb/c nude mouse (female, 7 weeks old, CLEA Japan, Inc.), and its ascitic fluid was collected. The antibody was purified from the ascitic fluid using protein G and used in subsequent research.

Next, the activity of the obtained antibody was evaluated. As for inhibitory activity, lamina propria cells of the large intestine were collected and then reacted at $2 \times 10^6$ cells with 50 ng/50 µl CHL-1 protein (Fc tag) (Sino Biological Inc) at 4° C. for 30 minutes. For this reaction, 1 µg/50 µl antibody to CHL1 (336) was added. Then, the inhibition of the adsorption reaction of the CHL-1 protein was verified by flow cytometry using goat anti-human IgG (H+L) secondary antibody, Alexa 647 conjugate (Life Technologies Corp.: A21445). The results were as shown in the upper and lower left panels of FIG. 10.

Figure 10:
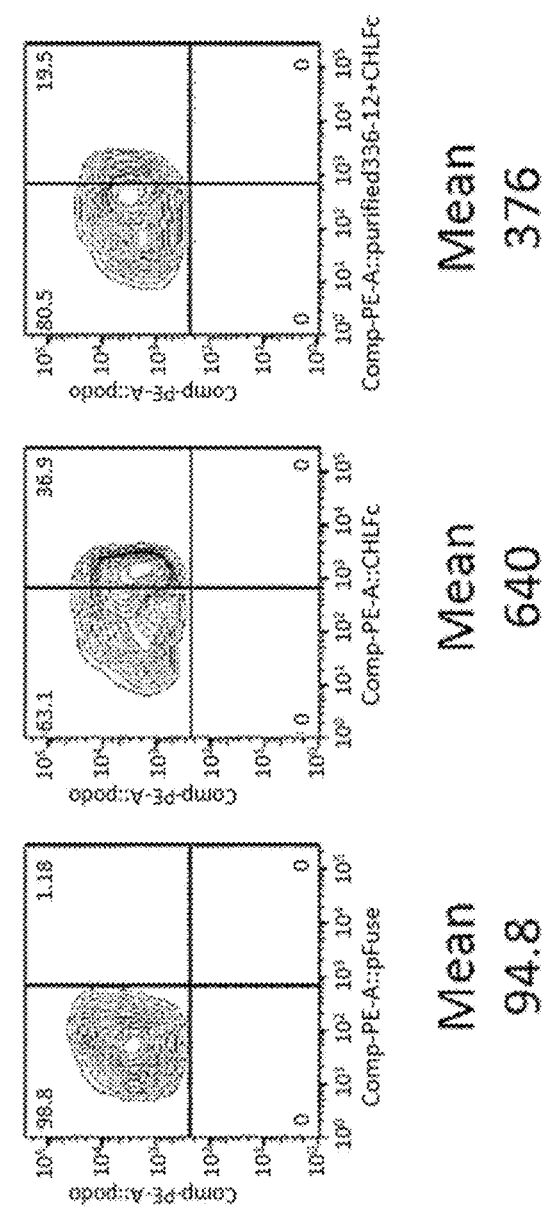
FIG. 10 is a diagram showing that the 336 antibody can neutralize the binding of the CHL1 protein to a cell.
Figure 10:
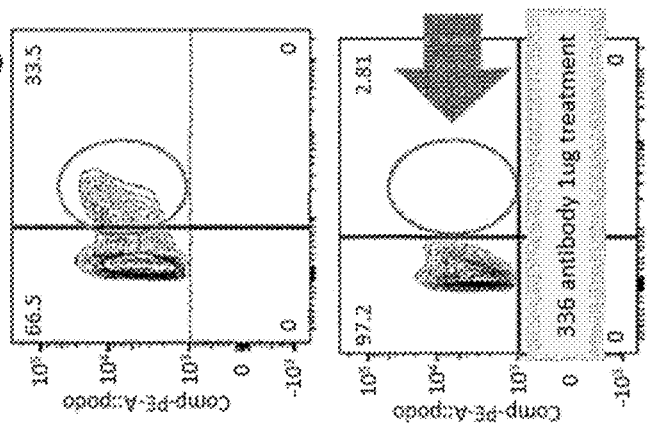

As shown in the left panels of FIG. 10, in the absence of the 336 antibody, the lamina propria cell of the large intestine bound to CHL1, and the Fc tag on cell surface was able to be detected with the antibody (left upper panel of FIG. 10). On the other hand, in the presence of the 336 antibody, the binding between the lamina propria cell of the large intestine and the CHL1 protein was blocked by the 336 antibody (left lower panel of FIG. 10). Likewise, the 336 antibody inhibited the binding of the CHL1 protein to the lamina propria cell of the large intestine in the presence of 75 ng of CHL1-Fc (FIG. 10, right).

The amino acid sequence of the heavy chain variable region and the amino acid sequence of the light chain variable region of the obtained 336 antibody will be shown below. CDR-H1 to -H3 represent CDR1 to CDR3, respectively, of the heavy chain variable region (SEQ ID NOs: 1 to 3, respectively). CDR-L1 to -L3 represent CDR1 to CDR3, respectively, of the light chain variable region (SEQ ID NOs: 5 to 7, respectively).

The heavy chain variable region of the 336 antibody has a signal sequence (MKCRWIILFLMAVATGVNS; SEQ ID NO: 9) at its N terminus, the description of which is omitted below. The light chain variable region of the 336 antibody has a signal sequence (MDFRVQIFSFLLVSITVIVSSG; SEQ ID NO: 10) at its N terminus, the description of which is omitted below.

[Formula 1]
336 antibody heavy chain variable region
Heavy chain
```
                                            (SEQ ID NO: 4)
         10         20         30         40
EVQLQQSGPE LQRPGASVKL SCKASGYPFT EYYIYWMKQR
                                  CDR-H1

50         60         70         80
PKQGLELIGR IDPEDGSTDY VEKFKNKATL TADTSSNTAY
         CDR-H2

90        100        110        120
MQLSSLTSED TATYFCARAL QGFAYWGQGT LVTVSS
                  CDR-H3

130        140        150
```

[Formula 2]
336 antibody light chain variable region
Light chain
```
                                            (SEQ ID NO: 8)
         10         20         30         40
EIVLTQSPTT MAASPGEKVT LTCRASSSVS YMYWYLQKSG
                        CDR-L1

50         60         70         80
TSPKLWIYDT SRLASGIPDR FSGSGSGTSY SLTISSMETE
         CDR-L2

90        100        110        120
DTATYYCQQG GSYPYTFGAG TKLELKRA
         CDR-L3

130        140        150
```

In an in vivo inhibition experiment, enteritis was induced in 8-week-old male C57Bl/6 mice (CLEA Japan, Inc.) using 2.25% aqueous dextran sodium sulfate solution. The 336 antibody (n=4) or a control antibody (polyclonal rat IgG; Bio X Cell: BE0094) (n=4) was intraperitoneally administered at 250 μg/dose on consecutive days from day 6 to day 10. As for change in body weight, their body weights were measured around 16:00 every day. On day 11, the mice were dissected. Typical photographs about the large intestine and HE (hematoxylin-eosin)-stained large intestine are shown. The results were as shown in FIG. 11.

Figure 11:
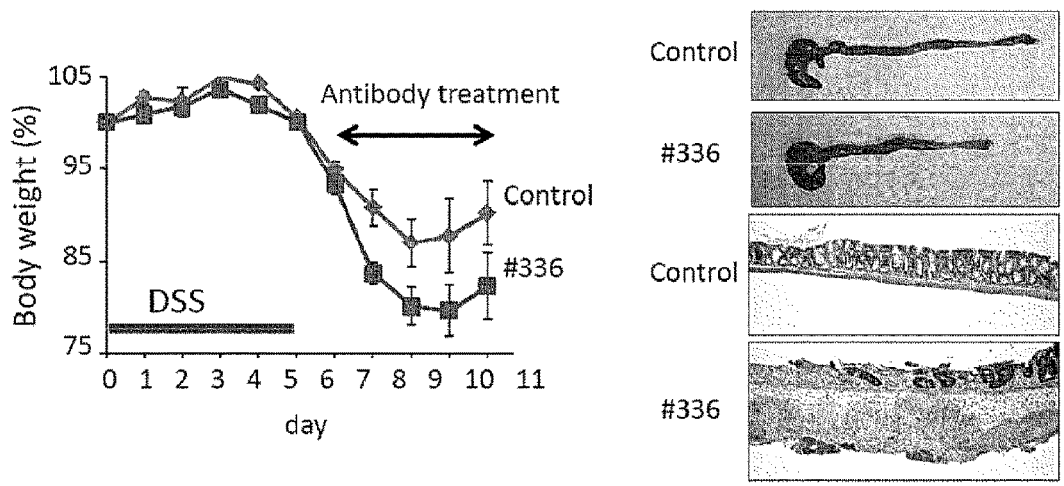
FIG. 11 is a diagram showing that the 336 antibody which can neutralize the binding of the CHL1 protein to a cell delays body weight recovery at the acute phase of inflammation (left graph of FIG. 11) and delays the healing of the intestinal mucosa (right photographs of FIG. 11).

As shown in FIG. 11, the 336 antibody delayed recovery from inflammation at the acute phase (left graph of FIG. 11). The results of HE staining shown in the right lower photograph of FIG. 11 also shows that the 336 antibody delayed recovery from inflammation at the acute phase. This demonstrated that an antibody that can block the binding of the CHL1 protein to a receptor on a cell membrane can suppress inflammation.

Example 6: Testing of Inflammation by Using CHL1 Expression Level as Index

Chronic enteritis (fibrosis) was induced in C57Bl/6 wild-type mice by repeated free drinking of 2.25% to 2.5% aqueous dextran sodium sulfate solution. On days 10 to 15, days 60 to 70, day 100, day 120, and 130 the CHL1 expression of fibroblasts in the lamina propria of the large intestine was analyzed by FACS. The CHL1 expression was analyzed by flow cytometry using anti-mouse CHL-1/L1CAM-2 monoclonal antibody (R&D Systems, Inc.)-APC goat anti-rat IgG (BioLegend, Inc.: 405407) and FACSCalibur (BD). The cells were labeled with antibodies to a blood cell marker CD45 and a fibroblast marker podoplanin. Then, CD45-negative podoplanin-positive fibroblasts were selected and analyzed for the expression of CHL1 on cell surface. The results were as shown in FIG. 12.

Figure 12:
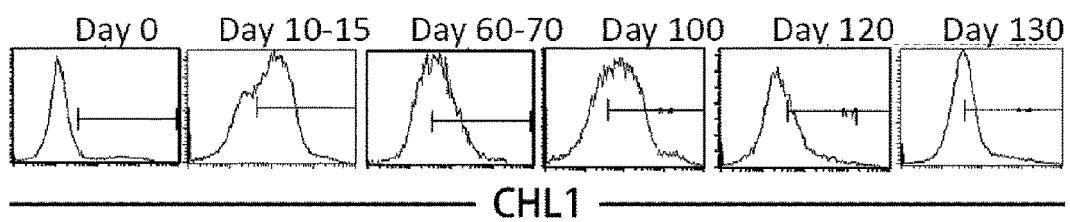
FIG. 12 is a diagram showing that the CHL1 protein is expressed in a sustained manner in fibroblasts even at the chronic phase of inflammation.

A shown in FIG. 12, it was demonstrated that neutrophil invasion serving as an index for acute inflammation was reduced while the expression was maintained even at the chronic phase of 60 days after the induction of enteritis. The expression of the CHL1 protein at the chronic phase can be used as an index for cell fibrosis.

Feces was harvested from mice having acute (n=12) or chronic inflammation (n=16) by use of an aqueous dextran sodium sulfate solution, and untreated mice (n=13), and a CHL1 level in the feces was analyzed. The experimental approach will be described below.

Day 1
1. A 96-well plate is coated by overnight incubation at 4° C. in the presence of the purified 336 antibody (1 μg/ml is added at 100 μL/well).

Day 2
1. The plate is washed three times with a washing buffer solution (0.05% Tween-PBS).
2. A blocking buffer solution (PBS containing 1% BSA) is added thereto (300 μL/well), followed by incubation at room temperature for at least 1 hour.
3. The plate is washed three times with a washing buffer solution.
4. 100 μl of a sample is added to each well (1 mg/10 μL PBS, and the plate is vortexed at 4° C. for 30 minutes and centrifuged at 15000 rpm (15 min), followed by the collection of a supernatant.

Overnight

Day 3
1. The plate is washed three times with a washing buffer solution.
2. The biotinylated 336 antibody is added (detection Ab: stock 1 mg/ml diluting solution: reagent diluent 1% BSA in PBS) (1 μg/ml is added at 100 μL/well), followed by incubation at room temperature for 2 hours.
3. The plate is washed three times with a washing buffer solution.
4. Streptavidin-HRP (R&D Systems, Inc., lot #310801/Part #893975) (dilution ratio: 1:40, 100 μL/well) is added, followed by incubation for 2 hours.
5. The plate is washed three times with a washing buffer solution.

6. A HRP substrate is added (100 μl/well), followed by incubation for 45 minutes.
7. A reaction stopping solution (50 μL of $H_2SO_4$) is added.
8. Absorbance is measured (450 nm/570 nm).

Figure 13:
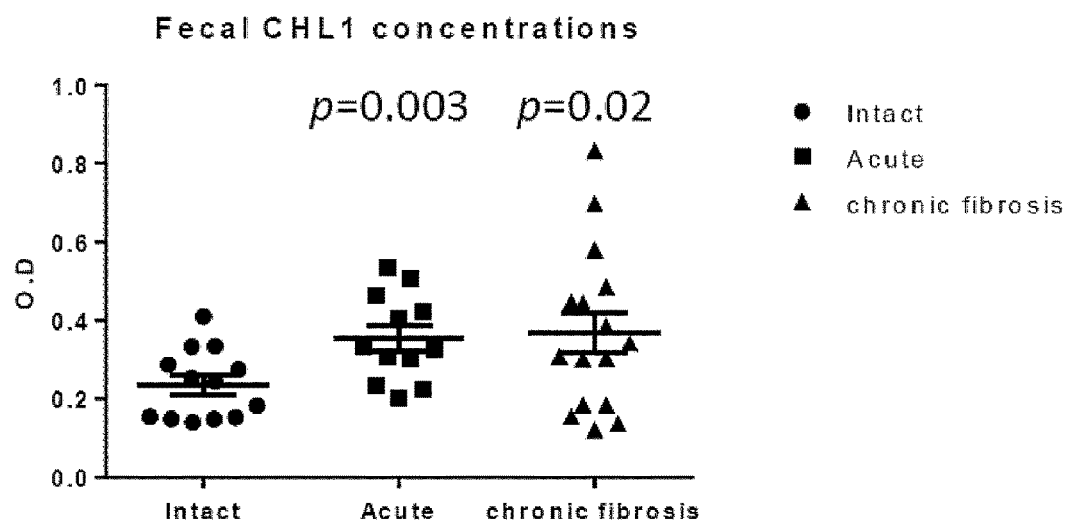
FIG. 13 is a diagram showing that the CHL1 protein is detected from the excrement of enteritis models (acute and chronic).

The results were as shown in FIG. 13. As shown in FIG. 13, the CHL1 level in the feces was statistically significantly higher in the mouse group with acute or chronic inflammation than that in usual mice. This indicated that the presence or absence of inflammation may be determined by measuring the protein level of CHL1 using feces. These results also indicated that CHL1 is capable of functioning as a secreted factor.

Example 7: Therapeutic Significance of Antibody to CHL1 in Fibrosis Induction Process In this Example, the role of an antibody to CHL1 in a fibrosis induction process after acute inflammation was examined.

To mice with intestinal fibrosis induced by the repeated free drinking of an aqueous dextran sodium sulfate solution, the 336 antibody (250 μg/dose) was intraperitoneally administered on consecutive days when the mice recovered from weight loss (days 56 to 66) after the third run of the repeated free drinking. Polyclonal rat IgG (Bio X Cell: BE0094) was intraperitoneally administered as a control antibody. On day 67 or 68, the mice were dissected, and their large intestine tissues were collected. Then, paraffin sliced sections were prepared. Collagen deposition and the accumulation of activated fibroblasts and myofibroblasts were analyzed by Azan staining or staining with α-Smooth Muscle—Cy3™ antibody, Mouse monoclonal clone 1A4, purified from hybridoma cell culture (Sigma-Aldrich Co. LLC, C6198-100UL) (red) and DAPI (nucleus; blue). The results were as shown in FIG. 14.

Figure 14:
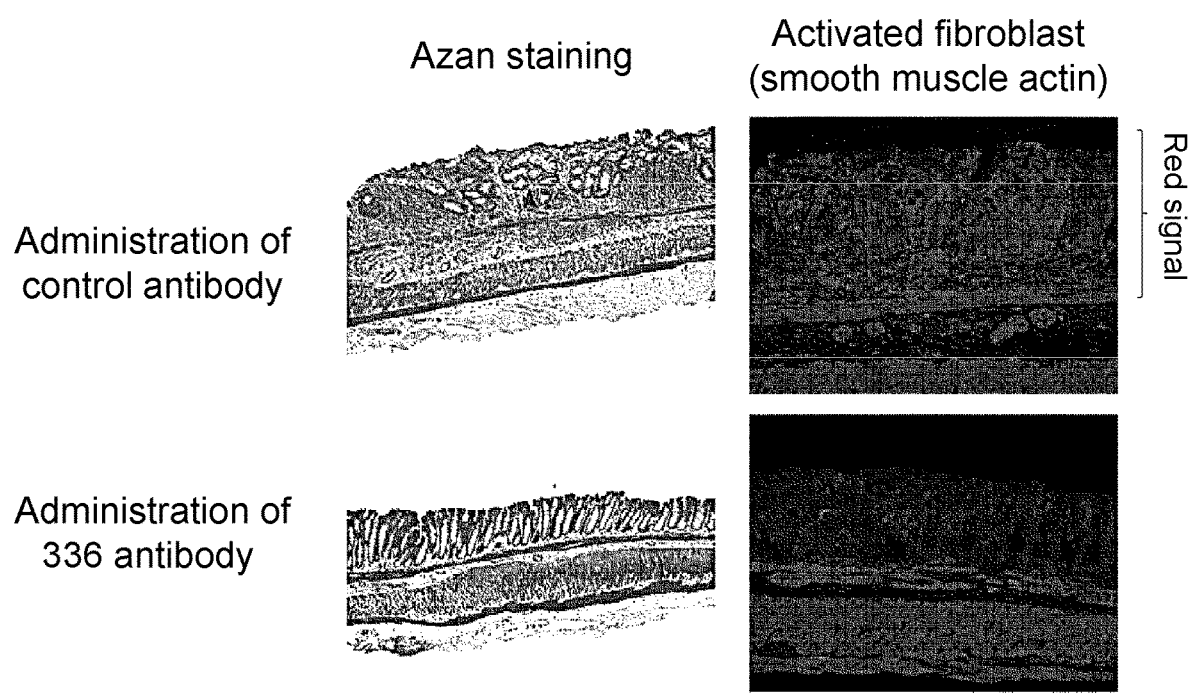
FIG. 14 is a diagram showing that an antibody to CHL1 suppresses collagen deposition and fibroblast activation in a fibrosis induction process at the chronic phase of inflammation.

As shown in FIG. 14, the 336 antibody, a monoclonal antibody to CHL1, suppressed collagen deposition in the tissue after acute inflammation, and suppressed fibroblast activation.

Examples described above indicated that the antibody to CHL1 suppresses inflammation caused by CHL1. Examples described above also demonstrated that when inflammation is suppressed at the chronic phase, collagen deposition and fibroblast activation can be suppressed, and fibrosis in an inflammatory tissue can thereby be suppressed.

SEQ ID NO: 1: Amino acid sequence of the heavy chain CDR1 of a 336 antibody
SEQ ID NO: 2: Amino acid sequence of the heavy chain CDR2 of the 336 antibody
SEQ ID NO: 3: Amino acid sequence of the heavy chain CDR3 of the 336 antibody
SEQ ID NO: 4: Amino acid sequence of the heavy chain variable region of the 336 antibody
SEQ ID NO: 5: Amino acid sequence of the light chain CDR1 of the 336 antibody
SEQ ID NO: 6: Amino acid sequence of the light chain CDR2 of the 336 antibody
SEQ ID NO: 7: Amino acid sequence of the light chain CDR3 of the 336 antibody
SEQ ID NO: 8: Amino acid sequence of the light chain variable region of the 336 antibody.

The invention claimed is:

1. A method for analyzing the presence or absence of inflammation in a tissue in a subject, comprising determining the presence of secreted CHL1 protein in the tissue, a body fluid, or excrement obtained from the subject by using an antibody or an antigen-binding fragment thereof that binds to secreted CHL1 protein,
wherein the antibody and the fragment has a heavy chain variable region having heavy chain CDR1 having the amino acid sequence set forth in SEQ ID NO: 1, heavy chain CDR2 having the amino acid sequence set forth in SEQ ID NO: 2 and heavy chain CDR3 having the amino acid sequence set forth in SEQ ID NO: 3, and a light chain variable region having light chain CDR1 having the amino acid sequence set forth in SEQ ID NO: 5, light chain CDR2 having the amino acid sequence set forth in SEQ ID NO: 6 and light chain CDR3 having the amino acid sequence set forth in SEQ ID NO: 7.

2. The method according to claim 1, wherein the excrement is a feces and the tissue is intestine.

3. The method of claim 1, wherein the subject has a risk of developing tissue fibrosis in the tissue.

4. The method of claim 1, further comprising administering to the subject an antibody or an antigen-binding fragment thereof that binds to secreted CHL1 protein and can neutralizes the binding of the secreted CHL1 protein to a non-immune and non-epithelial non-hemocyte cell of the lamina propria and a submucosal layer,
wherein the antibody and the fragment has a heavy chain variable region having heavy chain CDR1 having the amino acid sequence set forth in SEQ ID NO: 1, heavy chain CDR2 having the amino acid sequence set forth in SEQ ID NO: 2 and heavy chain CDR3 having the amino acid sequence set forth in SEQ ID NO: 3, and a light chain variable region having light chain CDR1 having the amino acid sequence set forth in SEQ ID NO: 5, light chain CDR2 having the amino acid sequence set forth in SEQ ID NO: 6 and light chain CDR3 having the amino acid sequence set forth in SEQ ID NO: 7.

5. The method of claim 2, further comprising administering to the subject an antibody or an antigen-binding fragment thereof that binds to secreted CHL1 protein and can neutralizes the binding of the secreted CHL1 protein to a non-immune and non-epithelial non-hemocyte cell of the lamina propria and a submucosal layer,
  wherein the antibody and the fragment has a heavy chain variable region having heavy chain CDR1 having the amino acid sequence set forth in SEQ ID NO: 1, heavy chain CDR2 having the amino acid sequence set forth in SEQ ID NO: 2 and heavy chain CDR3 having the amino acid sequence set forth in SEQ ID NO: 3, and a light chain variable region having light chain CDR1 having the amino acid sequence set forth in SEQ ID NO: 5, light chain CDR2 having the amino acid sequence set forth in SEQ ID NO: 6 and light chain CDR3 having the amino acid sequence set forth in SEQ ID NO: 7.

6. A method of detecting inflammation in an intestine in a subject, comprising detecting CHL1 protein in a feces obtained from the subject, and determining that inflammation is detected in the intestine in a subject, based on the presence of CHL1 protein, and
  administering to the subject an antibody or an antigen-binding fragment thereof that binds to secreted CHL1 protein and can neutralizes the binding of the secreted CHL1 protein to a non-immune and non-epithelial non-hemocyte cell of the lamina propria and a submucosal layer,
  wherein the antibody and the fragment has a heavy chain variable region having heavy chain CDR1 having the amino acid sequence set forth in SEQ ID NO: 1, heavy chain CDR2 having the amino acid sequence set forth in SEQ ID NO: 2 and heavy chain CDR3 having the amino acid sequence set forth in SEQ ID NO: 3, and a light chain variable region having light chain CDR1 having the amino acid sequence set forth in SEQ ID NO: 5, light chain CDR2 having the amino acid sequence set forth in SEQ ID NO: 6 and light chain CDR3 having the amino acid sequence set forth in SEQ ID NO: 7.

* * * * *

SEQUENCE LISTING

```
<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: 336 H-CDR1

<400> SEQUENCE: 1

Glu Tyr Tyr Ile Tyr
1               5

<210> SEQ ID NO 2
<211> LENGTH: 17
<212> TYPE: PRT
<213> ORGANISM: Artificial Sequence
<220> FEATURE:
<223> OTHER INFORMATION: 336 H-CDR2

<400> SEQUENCE: 2

Arg Ile Asp Pro Glu Asp Gly Ser Thr Asp Tyr Val Glu Lys Phe Lys
1               5                   10                  15

Asn

<210> SEQ ID NO 3
<211> LENGTH: 7
<212> TYPE: PRT
<213> ORGANISM: Artificial Sequence
<220> FEATURE:
<223> OTHER INFORMATION: 336 H-CDR3

<400> SEQUENCE: 3
```

```
Ala Leu Gln Gly Phe Ala Tyr
1               5

<210> SEQ ID NO 4
<211> LENGTH: 116
<212> TYPE: PRT
<213> ORGANISM: Artificial Sequence
<220> FEATURE:
<223> OTHER INFORMATION: 336 VH

<400> SEQUENCE: 4

Glu Val Gln Leu Gln Gln Ser Gly Pro Glu Leu Gln Arg Pro Gly Ala
1               5                   10                  15

Ser Val Lys Leu Ser Cys Lys Ala Ser Gly Tyr Pro Phe Thr Glu Tyr
            20                  25                  30

Tyr Ile Tyr Trp Met Lys Gln Arg Pro Lys Gln Gly Leu Glu Leu Ile
        35                  40                  45

Gly Arg Ile Asp Pro Glu Asp Gly Ser Thr Asp Tyr Val Glu Lys Phe
    50                  55                  60

Lys Asn Lys Ala Thr Leu Thr Ala Asp Thr Ser Ser Asn Thr Ala Tyr
65                  70                  75                  80

Met Gln Leu Ser Ser Leu Thr Ser Glu Asp Thr Ala Thr Tyr Phe Cys
                85                  90                  95

Ala Arg Ala Leu Gln Gly Phe Ala Tyr Trp Gly Gln Gly Thr Leu Val
            100                 105                 110

Thr Val Ser Ser
        115

<210> SEQ ID NO 5
<211> LENGTH: 10
<212> TYPE: PRT
<213> ORGANISM: Artificial Sequence
<220> FEATURE:
<223> OTHER INFORMATION: 336 L-CDR1

<400> SEQUENCE: 5

Arg Ala Ser Ser Ser Val Ser Tyr Met Tyr
1               5                   10

<210> SEQ ID NO 6
<211> LENGTH: 7
<212> TYPE: PRT
<213> ORGANISM: Artificial Sequence
<220> FEATURE:
<223> OTHER INFORMATION: 336 L-CDR2

<400> SEQUENCE: 6

Asp Thr Ser Arg Leu Ala Ser
1               5

<210> SEQ ID NO 7
<211> LENGTH: 9
<212> TYPE: PRT
<213> ORGANISM: Artificial Sequence
<220> FEATURE:
<223> OTHER INFORMATION: 336 L-CDR3

<400> SEQUENCE: 7

Gln Gln Gly Gly Ser Tyr Pro Tyr Thr
1               5

<210> SEQ ID NO 8
```

```
<211> LENGTH: 108
<212> TYPE: PRT
<213> ORGANISM: Artificial Sequence
<220> FEATURE:
<223> OTHER INFORMATION: 336 VL

<400> SEQUENCE: 8

Glu Ile Val Leu Thr Gln Ser Pro Thr Thr Met Ala Ala Ser Pro Gly
1               5                   10                  15

Glu Lys Val Thr Leu Thr Cys Arg Ala Ser Ser Ser Val Ser Tyr Met
            20                  25                  30

Tyr Trp Tyr Leu Gln Lys Ser Gly Thr Ser Pro Lys Leu Trp Ile Tyr
        35                  40                  45

Asp Thr Ser Arg Leu Ala Ser Gly Ile Pro Asp Arg Phe Ser Gly Ser
    50                  55                  60

Gly Ser Gly Thr Ser Tyr Ser Leu Thr Ile Ser Ser Met Glu Thr Glu
65                  70                  75                  80

Asp Thr Ala Thr Tyr Tyr Cys Gln Gln Gly Gly Ser Tyr Pro Tyr Thr
                85                  90                  95

Phe Gly Ala Gly Thr Lys Leu Glu Leu Lys Arg Ala
            100                 105

<210> SEQ ID NO 9
<211> LENGTH: 19
<212> TYPE: PRT
<213> ORGANISM: Artificial Sequence
<220> FEATURE:
<223> OTHER INFORMATION: 336 VH Signal Sequence

<400> SEQUENCE: 9

Met Lys Cys Arg Trp Ile Ile Leu Phe Leu Met Ala Val Ala Thr
1               5                   10                  15

Gly Val Asn Ser

<210> SEQ ID NO 10
<211> LENGTH: 22
<212> TYPE: PRT
<213> ORGANISM: Artificial Sequence
<220> FEATURE:
<223> OTHER INFORMATION: 336 VL Signal Sequence

<400> SEQUENCE: 10

Met Asp Phe Arg Val Gln Ile Phe Ser Phe Leu Leu Val Ser Ile
1               5                   10                  15

Thr Val Ile Val Ser Ser Gly
            20
```